US00RE39657E

(19) United States
(12) Reissued Patent
Wakalopulos et al.

(10) Patent Number: US RE39,657 E
(45) Date of Reissued Patent: May 29, 2007

(54) STERILIZATION BY LOW ENERGY ELECTRON BEAM

(75) Inventors: George Wakalopulos, Torrance, CA (US); Eduardo R. Urgiles, Pasadena, CA (US); Peter Bond, Palos Verdes Estates, CA (US)

(73) Assignee: Ushio America, Inc., Cypress, CA (US)

(21) Appl. No.: 10/285,555

(22) Filed: Oct. 30, 2002

Related U.S. Patent Documents

Reissue of:
(64) Patent No.: 6,140,657
Issued: Oct. 31, 2000
Appl. No.: 09/270,966
Filed: Mar. 17, 1999

(51) Int. Cl.
*H01J 37/00* (2006.01)
*H01J 37/30* (2006.01)
*H01J 37/301* (2006.01)

(52) U.S. Cl. ..... 250/492.3; 250/492.1; 250/435

(58) Field of Classification Search ..... 250/492.3, 250/492.1, 435, 398
See application file for complete search history.

(56) References Cited

U.S. PATENT DOCUMENTS 3,780,308 A * 12/1973 Nablo ..... 250/492.3
3,942,017 A * 3/1976 Uehara et al. ..... 250/492.3
3,948,601 A * 4/1976 Fraser et al. ..... 21/54 R
4,652,763 A * 3/1987 Nablo ..... 250/492.3
4,801,427 A * 1/1989 Jacob ..... 422/23
5,120,972 A * 6/1992 Rangwalla et al. ..... 250/492.3
5,200,158 A * 4/1993 Jacob ..... 422/292
5,530,255 A * 6/1996 Lyons et al. ..... 250/492.3
5,612,588 A * 3/1997 Wakalopulos ..... 313/420
5,869,833 A 2/1999 Richardson et al.
5,962,995 A * 10/1999 Avnery ..... 315/506
6,139,796 A 10/2000 Kristiansson et al. ..... 422/22
6,575,084 B2 * 6/2003 Allen et al. ..... 99/451

FOREIGN PATENT DOCUMENTS

WO WO 97/07024 2/1997

* cited by examiner

*Primary Examiner*—Nikita Wells
(74) *Attorney, Agent, or Firm*—Paul Hasting LLP

(57) ABSTRACT

A sterilization apparatus wherein one or more electron beam tubes are used to direct electron beams into an ambient gaseous environment to create an electron plasma cloud into which non-sterile target objects may be moved. The electron plasma cloud is formed by interaction of the electron beam with the ambient atmosphere. Helium or other like gaseous may be used to expand the effective volume of the electron plasma cloud. Manipulators are used to move target objects in the electron plasma cloud, exposing non-sterile surfaces to the cloud and then joining the surfaces together where appropriate. The beam tube used to generate the electron beam has a thin low energy absorbing window which allows relatively low energy beams to be used, minimizing damage to materials within the surface of the target objects.

18 Claims, 6 Drawing Sheets

STERILIZATION BY LOW ENERGY ELECTRON BEAM

Matter enclosed in heavy brackets [ ] appears in the original patent but forms no part of this reissue specification; matter printed in italics indicates the additions made by reissue.

TECHNICAL FIELD

The invention relates to beam sterilization of surfaces of objects and, more particularly, to sterilization which relies mainly on electron beam interaction with surfaces of objects.

BACKGROUND ART

In the fields of medicine, pharmaceutical production, and food processing there is a critical need for sterilization to protect against the danger of harmful microorganisms. Most of the sterilization methods currently in use require the sterilizing agent to systemically permeate the article being sterilized. These methods include heat sterilization, where the object to be sterilized is subjected to heat and pressure, such as in an autoclave. The heat and pressure penetrates though the object being sterilized and after a sufficient time will kill the harmful microorganisms. Gases such as hydrogen peroxide or ethylene oxide have also been used to sterilize objects. For the complete sterilization of an object, the gas must permeate the entire object. An alternate sterilization method uses ionizing radiation, such as gamma-rays, x-rays, or energetic electrons for sterilization.

There are a number of target objects where exposure of the object to ionizing radiation would cause some deleterious effect on the target object. Examples include objects which would melt or degrade under heat sterilization, products that would degrade or react with chemical sterilizing agents, and materials that would be harmfully altered by exposure to high energy radiation, particularly ionizing radiation. It has previously been recognized that by confining ionizing radiation to the surface of a target object, the deleterious effect will not occur. On the other hand, most ionizing radiation is created by powerful beam generators, such as accelerators, and so a beam of ionizing radiation is inherently penetrating.

In U.S. Pat. No. 4,801,427 A. Jacob teaches a process for dry sterilization of medical devices subjected to an electrical discharge in a gaseous atmosphere to produce an active plasma. In one embodiment, Jacob teaches placement of articles on a conveyor belt which carries articles into an atmospheric pressure corona discharge gap operated in ambient air. The plasma is formed by a discharge between the grounded conveyor belt, acting as a cathode, and multiple needle-like nozzles, acting as anodes, which disperse a gas to be ionized, which may be an oxidizing gas such as oxygen or a reducing gas such as hydrogen. U.S. Pat. No. 5,200,158, also to A. Jacob teaches sterilization by exposure of an object to a gas plasma created by an electrical discharge in a sub-atmospheric gaseous atmosphere. Hydrogen, oxygen, nitrogen, and inert gasses are all taught as possible gasses to use in forming the plasma.

In contradistinction to the high energy approach of Jacob, U.S. Pat. No. 3,780,308 to S. Nablo teaches surface sterilization of objects using low energy electrons, even though a relatively high energy starting point is present. One of the advantages of low energy electrons is that bulk properties essential to the mechanics of the material sterilized are not affected. Nablo expanded upon his idea in U.S. Pat. No. 4,652,763 which teaches use of an electron beam producing electrons with energies that penetrate an outer layer but with insufficient energy to pierce an inner layer of target material.

A number of patents teach use of a gas plasma to effect surface sterilization. Fraser et al., in U.S. Pat. No. 3,948,601 teaches use of a continuous flow gas plasma supplied at very low pressure in a chamber with a target object to be sterilized. Cool plasma from a gas such as argon is continuously produced by exposure to a radio-frequency field.

One of the problems encountered in prior art sterilization devices involves three dimensional structures, such as vials, cuvettes and hoses. Sometimes such structures have contours which create shadows for a beam of ionizing radiation nor even a diffuse discharge such that reactive electrons or ions do not reach the contours and so there is little sterilization in such regions. One solution would be to rotate or otherwise turn the object being sterilized.

An object of the invention was to devise a sterilization apparatus for medical equipment and the like, having three dimensional structure, with full sterilization of contoured regions, using ionizing radiation, but not deleteriously effecting the target substance. Another object of the invention was to devise a sterilization apparatus which is more efficient than sterilization apparatus of the prior art.

SUMMARY OF THE INVENTION

The above object has been achieved with a sterilization chamber featuring one or more electron beam tubes generating low energy electron beams, preferably under 100 [kV] *keV*, in air or a surrounding gas at atmospheric pressure close to target objects to be sterilized. The low energy beams interact with air or surrounding gas to cause some ionization but a substantial fraction of the beam energy is delivered to the surface of a target object causing the object to be sterilized. A multiplicity of beam tubes may be used to eliminate shadows in cases where the target object has complex surface contours. Each tube has a stripe shaped beam which forms a plasma cloud in the beam path a short distance from a window in the beam tube by interaction of the electron beam with the ambient environment. Unlike metal foil windows of the prior art which cause high beam energy losses, the window of the beam tube used herein is preferably a thin semiconductor window which reduces losses in a high energy electron beam.

A manipulator, such as a robot arm or a glove box arm, moves target objects into a reactive volume of charged particles. It has been found that a sheath of helium gas, around the reactive volume, will enlarge the reactive volume by making a larger plasma cloud, consequently expanding the effective range of the beam. The sheath of helium gas is introduced by one or more nozzles near the window of the beam tube. Helium and surrounding oxygen atoms become excited by encounters with electrons, with some helium atoms becoming ionized and the oxygen converted to ozone. The positive ions of helium and the ozone contribute to the sterilization effectiveness of energetic electrons in breaking down proteinaceous material found in biological substances thereby sterilizing the substances. The zone of interacting electrons, helium and ozone atoms is termed a "plasma cloud" which is a volumetric zone where electrons and activated helium are mixing. Without introduction of helium an electron beam "plasma cloud" can still exist, but its effective range is limited to a space quite close to the window of the electron beam tube. As helium is introduced, the volume of the active species, electrons and helium ions, increases, thereby increasing the volume of the plasma cloud. Helium can be introduced by a nozzle directed at the electron beam emerging from the electron beam tube or by an annular nozzle coaxial with the beam tube.

A plurality of electron beam tubes can be arranged in a spatial pattern to create a composite plasma cloud which will eliminate any hidden surfaces or "shadows" of three dimensional objects that have complex surfaces. Also, a plurality of electron beam tubes can be arranged in patterns which would cover a large two dimensional area. For example, a triangular pattern of electron beam tubes would cover a large circular or triangular pattern on a flat surface, compared to the coverage of a single beam tube.

BEST MODE FOR CARRYING OUT THE INVENTION

Figure 1:
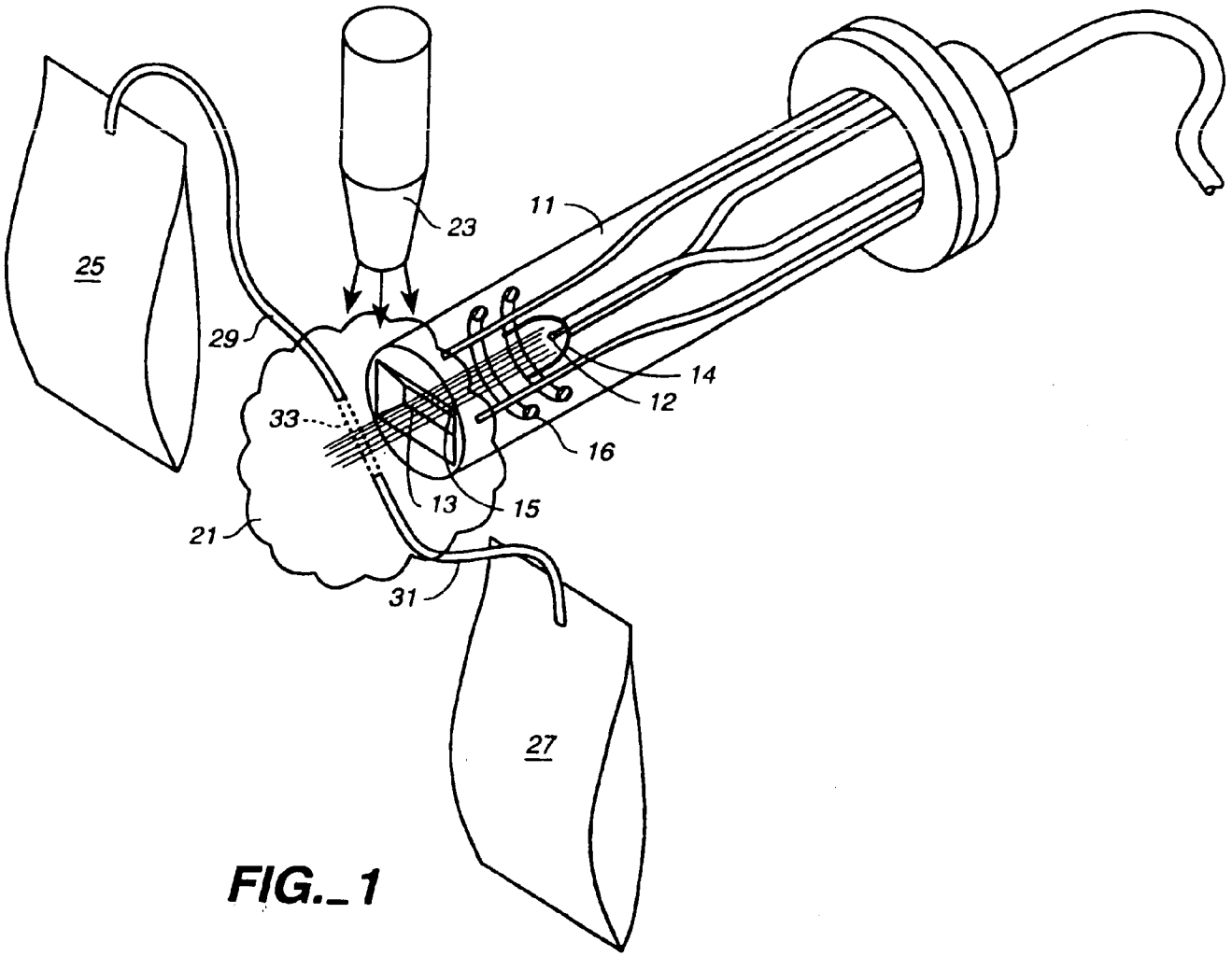
FIG. 1 is a perspective plan view of the sterilization apparatus of the present invention.

With reference to FIG. 1, an electron beam tube 11 is shown to have a window 13 through which a beam 15 emerges. Beam 15 is generated from a cathode 12 in front of an electrostatic focusing structure 14 and is further focused by a magnetic field generated by the helical coil 16. The detailed structure of beam tube 11 may be found in U.S. Pat. No. 5,612,588 to G. Wakalopulos, assigned to the assignee of the present invention. The thin window is only a few micrometers in thickness, or less, so that there is very little beam energy loss in penetrating the window. The window is preferably made of a material having a low atomic number so that electrons can readily penetrate the material, but gas molecules can not. This allows the interior of the tube to be at vacuum pressure while the outside of the tube is at ambient pressure, usually atmospheric pressure. The window is maintained at ground potential for safety reasons, while the cathode is maintained at a negative potential, for example −50 (kV) relative to the electrical potential of the window. If approximately 50% of the beam energy is lost in collisions with gas molecules outside of window 13, almost half the original beam energy will remain for delivery to a target surface. Such an electron energy level is sufficient for surface sterilization of various materials, but is insufficient to penetrate the surface of most target materials for more than a few micrometers. This is because unlike the thin tube window, the target materials are higher molecular weight structures which the low energy beam cannot penetrate to any appreciable depth.

Beam 15 is seen to be directed out of the window toward tubing 29 and 31 for an operation which involves filling bag 27 from a reservoir bag 25. Such a fill operation requires that the tubing from each bag be cut, connected for the filling operation, disconnected and the tubes resealed. In order to perform this operation, the size of window 13 is sufficiently large to create a plasma cloud consisting of the electrons in beam 15 and ionized gas from the ambient environment. Additionally, a nozzle 23 from a light inert gas supply, such as a helium tank, directs gas toward the beam and has the effect of expanding the effective volume of the plasma cloud as some helium atoms become ionized. The helium nozzle 23 can be used to shape the direction of the beam as well as to confine the beam to a desired location depending upon the nozzle design and configuration. Window 13 is seen to have a stripe shape, i.e. oblong, with a long dimension aligned so that the emerging electron beam has a corresponding stripe shape aligned with the linear dimension of the tubing to be connected. A typical width for window 13 is in the range of 1 to 3 centimeters.

Figure 2:
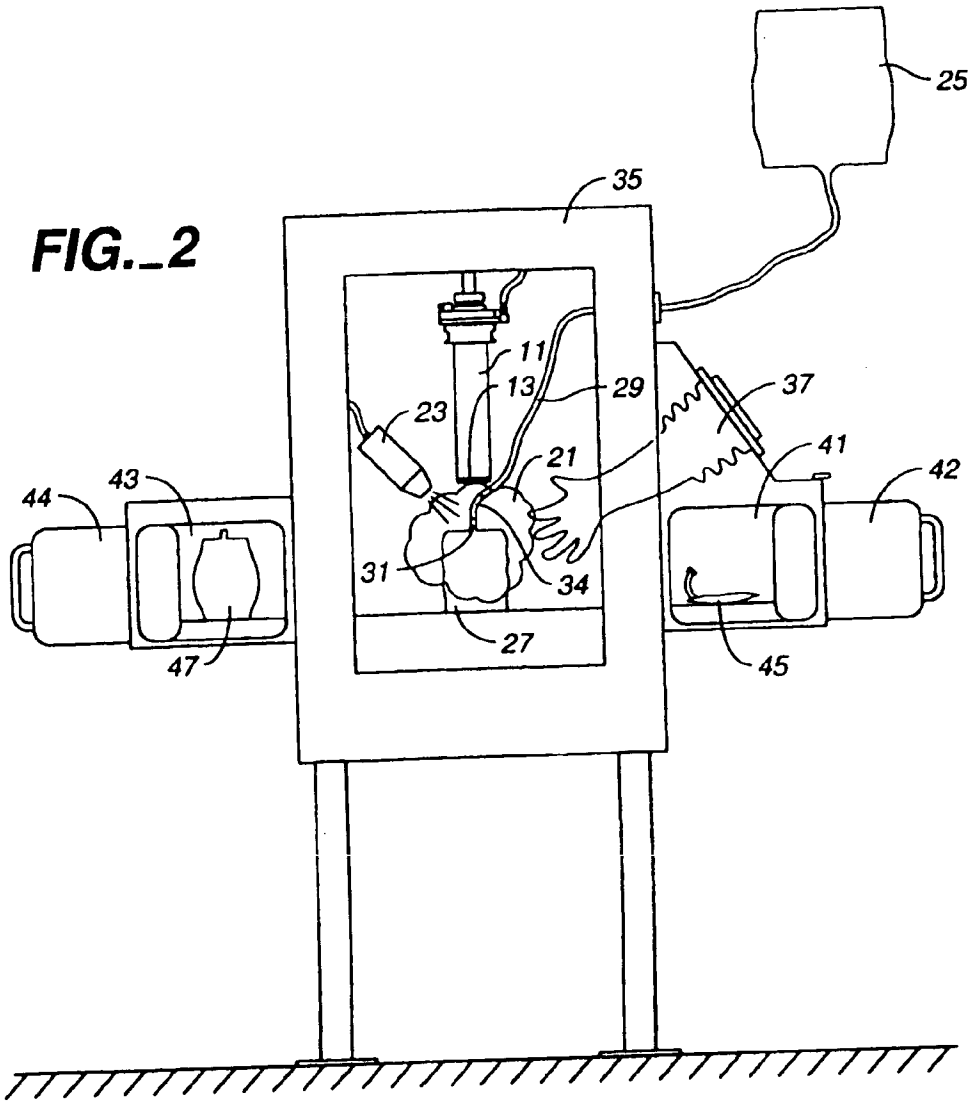
FIG. 2 is an elevational plan view of a sterilization machine for filling liquid bags employing the apparatus shown in FIG. 1.

A bag filling operation may be seen with reference to FIG. 2. A chamber 35 is equipped with beam tube 11 with window 13 approximately 1 to 2 inches from a target zone 34 where sterilization is to occur. A plasma cloud 21 is generated in the volume surrounding the surfaces to be sterilized at target zone 34. In order to carry out the cutting of tubing 29 for joining to tubing 31 a manipulator, such as a glove box arm 37 is used to handle the cutting, connecting and resealing operation. Unfilled sterile liquid bag 45 is placed in loading chamber 41 by using door 42. A port in the chamber 35 allows passage of the bag into the central interior of the chamber and maintains the ionizing radiation inside. Once a bag is filled, the glove box hand 37 or a conveyor mechanism may move the sterilized bag through another port in the chamber to the position indicated by the filled sterile liquid bag 47 in the unloading chamber 43. Door 44 allows access in removal of filled sterile bags after the beam tube is turned off.

Figure 3:
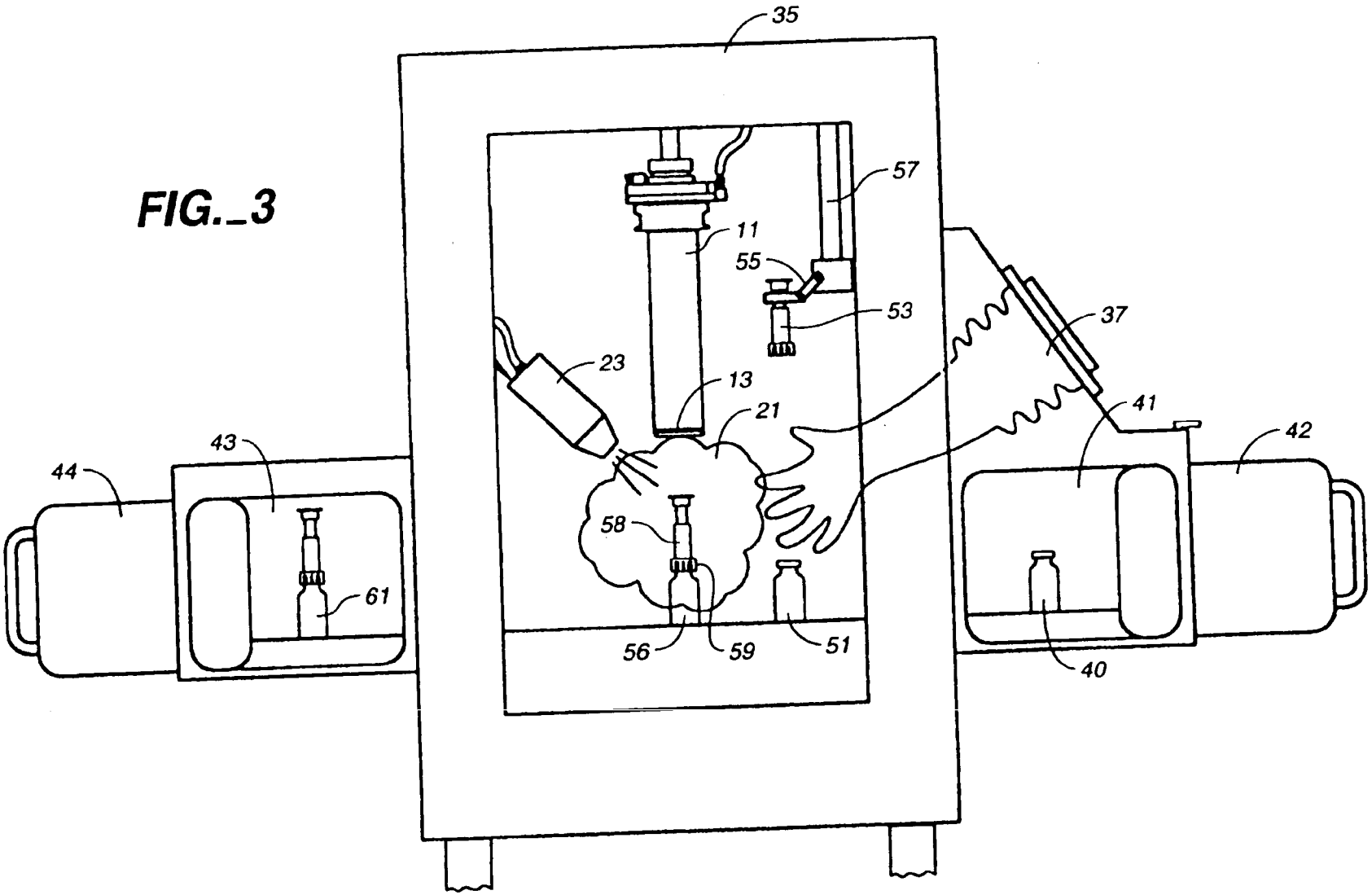
FIG. 3 is an elevational plan view of a sterilization machine for connecting two vials employing the apparatus shown in FIG. 1.

In FIG. 3, chamber 35 is seen to have been tube 11 pointed toward a pair of structures including a vial 56 and a syringe module 58 which have been brought together at a joint 59. Prior to joining, the structures are exposed to plasma cloud 21 generated by an electron beam tube 11. Glove box hand 37 moves an empty vial 51 into the vicinity of plasma cloud 21. A robot arm 57 with a hand 55 moves a syringe module 53 also into the plasma cloud. The vial 51 and the syringe module 53 have ends which are sterilized in the cloud and then the two modules are joined as exemplified by the vial 56 and the syringe module 58. The helium nozzle 23 controls the size of the plasma cloud, allowing expansion of the cloud by increased amounts of helium. The amount of helium which is injected can expand the cloud from approximately a 2 inch diameter to a 4 or 5 inch diameter. Further expansion may lead to an unwanted dilution of the electron beam. The size of the plasma cloud with various helium flows and pressures must be established by calibration with test surfaces. In most cases, the electron beam tube runs continuously, but the tube could be operated on an intermittent basis if desired, especially if cooling of thin window 13 becomes an issue. While FIG. 3 shows a glove box scene and a robot arm as a pair of manipulators, a single manipulator may be used, operating on one object at a time. Robotic manipulators have the advantage of speed where large numbers of identical objects are to be sterilized. Glove box arm manipulators are advantageous where the target objects are different or small numbers or different sizes of target objects are involved. The robotic manipulator could be a standard pick and place machine.

An empty vial 40 is seen to be placed in chamber 41 through the open door 42. This vial is filled with a sterile liquid, but the cap is unsterilized and so there is some risk that a syringe module might contaminate the sterile liquid either through the syringe itself or through the unsterilized cap. By bringing both the syringe module and the unsterilized cap into the electron plasma cloud, both members to be joined become sterilized, with the joint between the vial and the syringe being sterilized.

The environment within chamber 35 is an ambient air environment at atmospheric pressure and ambient temperature. For a beam current of one milliamp, emerging from window 13 at 50 [kV] *keV*, a helium flow velocity from nozzle 23 of a few liters per minute is appropriate.

Figure 6:
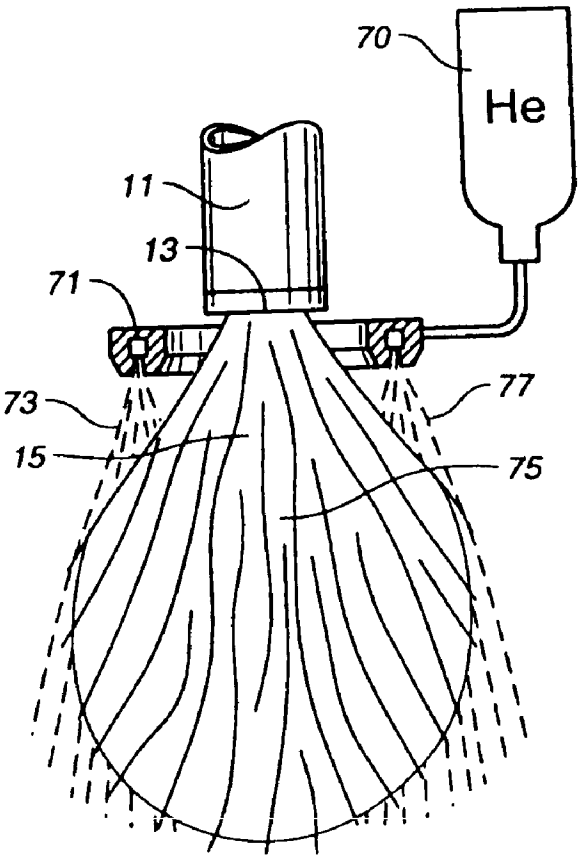
FIGS. 5 and 6 are side plan views of an electron beam window in combination with a gas nozzle for use in the sterilization apparatus of the present invention, creating a plasma cloud.
Figure 5:
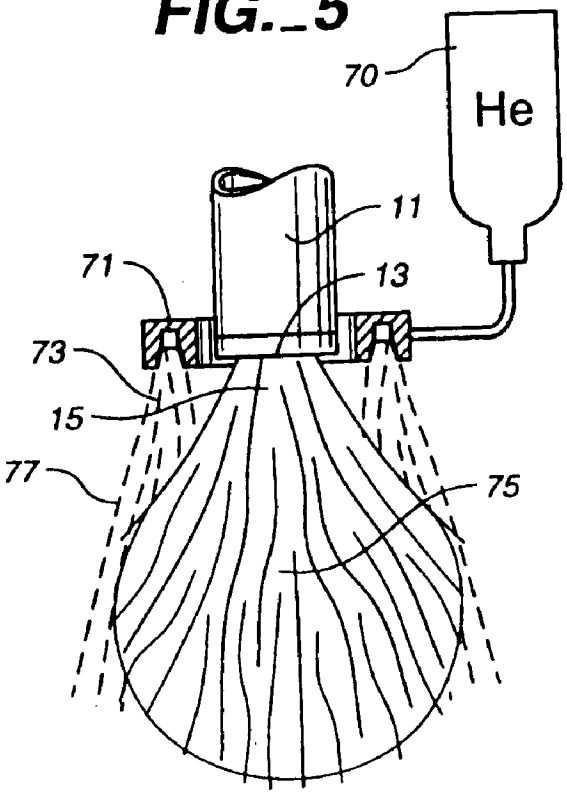
Figure 4:
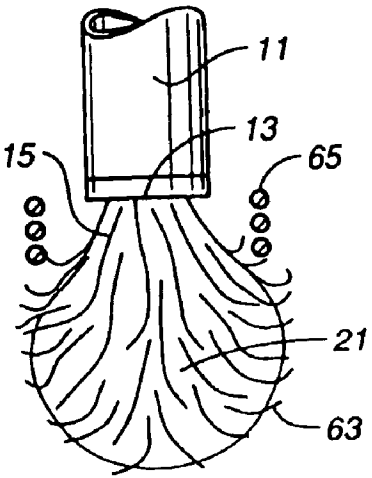
FIG. 4 is a side plan vie of an electron beam used in the sterilization apparatus shown in FIG. 1, creating a plasma cloud.

With reference to FIG. 4, an end of beam tube 11 is seen having a plasma cloud 21 beyond window 13. The plasma cloud is formed by the interaction of electrons from beam 15 with molecules of air. The electrons collide with molecules of oxygen and nitrogen, ionizing some of them. The ionized molecules together with the electrons remaining in the beam serve as agents of sterilization. The mechanism of sterilization is not precisely known, but it is thought that the electrons and energetic ions break down proteinaceous material, involving molecules of complex shape and function. Proteinaceous material on the target substances have been found to be sufficiently damaged by the plasma cloud that the surface associated with such material is considered sterile. Optionally, the shape of the plasma cloud may be adjusted by a magnetic field generated by a coil 65 outside of beam tube 11. Another coil, inside of the beam tube 11 may adjust the size and shape of the beam before it leaves the beam tube. A magnetic coil, such as coil 65 may also be used to steer the emerging electron beam 15 in a manner such that the plasma cloud may be moved. In FIGS. 5 and 6, a nozzle 71, connected to a gas supply tank 70, may be seen injecting a stream of a light inert gas 73, preferably helium to create a skirt 77, leading to an expanded plasma cloud 75, compared to that of FIG. 4 where the light gas was not injected. Nozzle 71 emits gas in a pattern surrounding the beam 15, serving to confine the electron beam as well as expanding the distance of the plasma cloud from the window 13.

Figure 7:
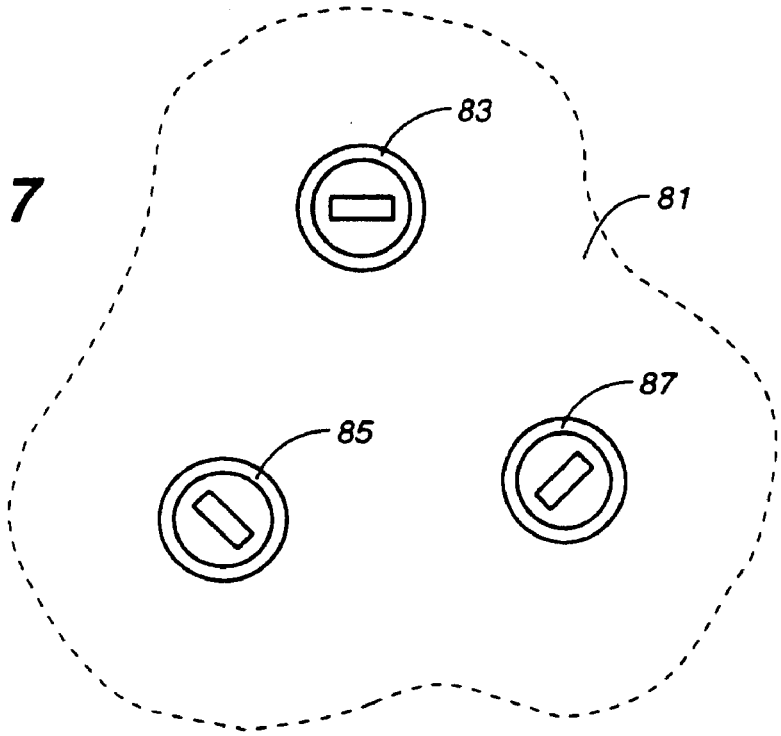
FIG. 7 is a front plan view of a plurality of electron beam tubes arranged in a pattern for creating a plasma cloud in accord with the present invention.
Figure 8:
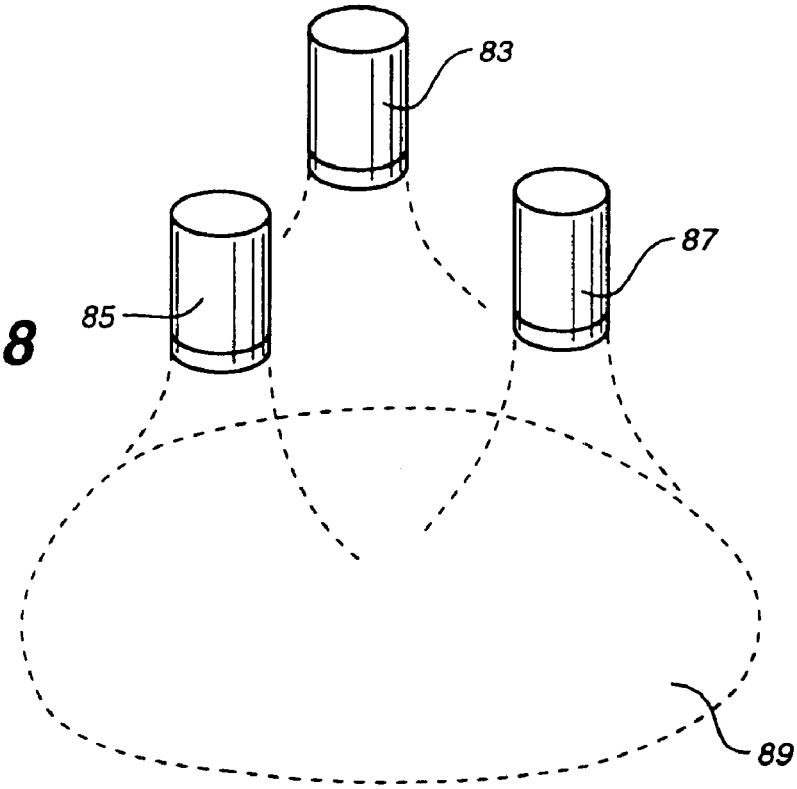
FIG. 8 is a side plan view of the apparatus of FIG. 7.

FIGS. 7 and 8 show a composite electron beam tube arrangement 81 having electron beam tubes 83, 85 and 87 arranged in a triangular pattern. These tubes can irradiate a larger two-dimensional zone, compared to a single tube, or can be used to create a larger three-dimensional plasma cloud than a single tube. By using a multiplicity of tubes and nozzles, shadow areas may be eliminated in objects having a complex shape. The three tubes need not be aligned in triangular pattern as shown in FIGS. 7 and 8, but may be at places most advantageous for eliminating non-sterile shadows in target objects having surfaces with complex shapes.

Although helium gas has been mentioned as the preferred gas for expanding a plasma cloud, other light gasses, with atomic numbers less than oxygen, would also work. In particular, it has been found that if argon is used, argon becomes excited and persists as in a metastable state for a brief period of time which allows sterilization to occur by a different mechanism than ionized atoms.

Figure 10:
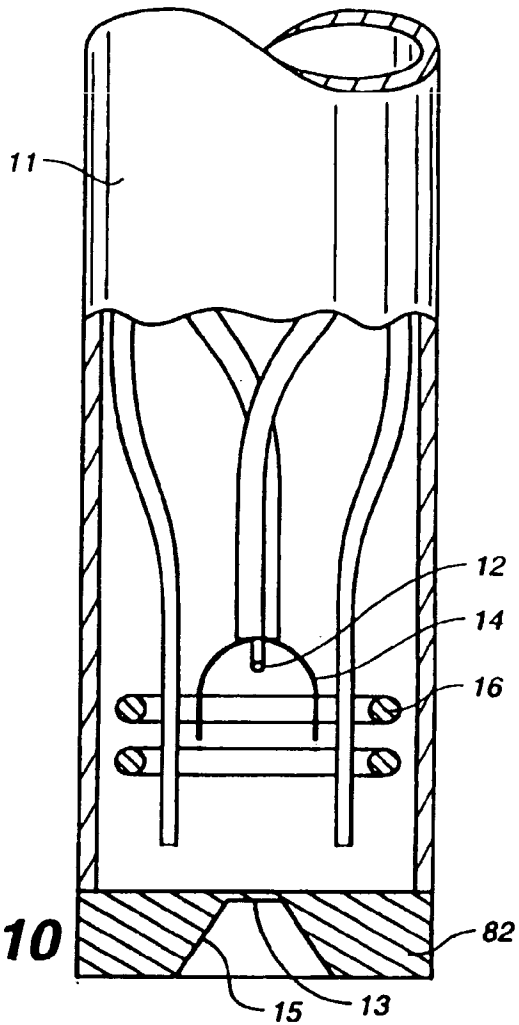
FIG. 10 is a side plan partial view of an electron beam tube used in the apparatus of FIG. 1.
Figure 9:
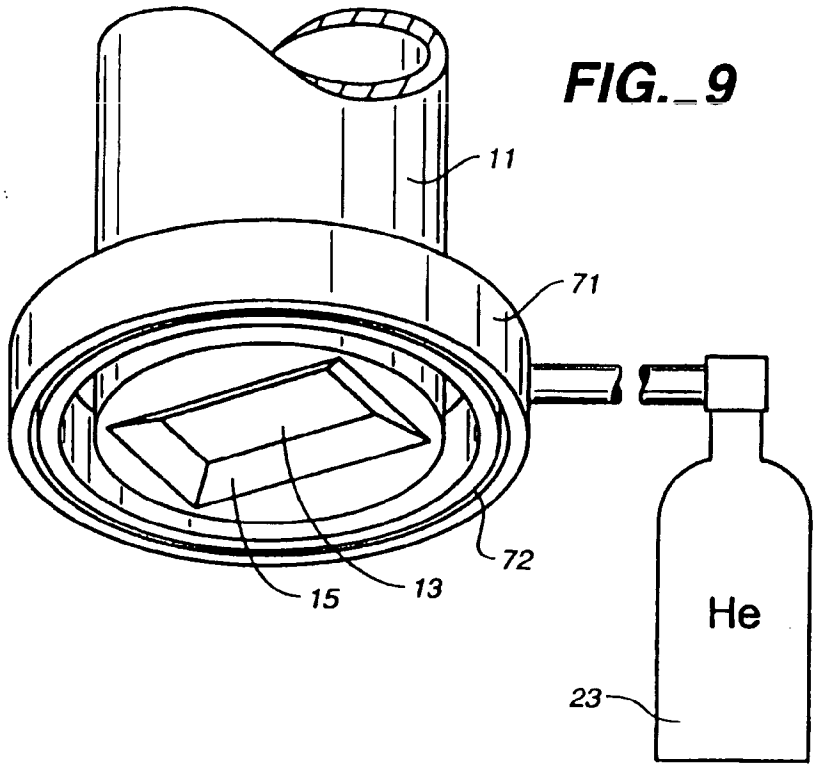
FIG. 9 is a detail of a gas injection nozzle fitting around an electron beam tube window in accord with the present invention.

In FIG. 9, a detail of electron beam tube 11 shows an annular nozzle 71 surrounding the window end of beam tube 11. Electrons emerge through window 13, but gas from a supply tank 23, introduced into the annular nozzle, emerges through an annular slit 72 to provide gas sheath around the beam emerging through window 13. Window 13 is seen to be recessed with respect to the remainder of the face of the electron beam tube, indicating the thinness of the window. This aspect is more clearly seen in FIG. 10 where the output of the beam tube is seen to have a face 82 made of a single crystal semiconductor material, such as silicon. The limit on the thinness of the window is the need to avoid stress between the vacuum environment inside of tube 11 and the ambient environment outside. As previously mentioned, cathode 12 produces electrons which are focused by the structure 14 and the helical coil 16 to be directed toward the window 13. Although the electron beam can be made to sweep by the coil inside the tube, the most common configuration is to enlarge the beam size to occupy the full extend of the window. Material on either side of the window carries away any heat dissipated by beam passage through the window. Such beam tubes are commercially available from American International Technologies, Inc. of Torrance, Calif.

What is claimed is:

1. A sterilization apparatus comprising, an electron beam tube having a window permitting emergence of an electron beam from said tube into an ambient gaseous environment while preserving a vacuum environment in the tube, the electron beam having a trajectory within a plasma cloud defining a reactive volume stimulated by interaction of the electron beam with the ambient environment, with a beam energy less than 100 [kV] *keV* at the target, and a moveable member manipulating objects in a plurality of directions within the reactive volume wherein the manipulated objects are sterilized.

2. The apparatus of claim 1 further defined by a nozzle surrounding a window end of said beam tube and injecting a gas directed at the electron beam.

3. The apparatus of claim 1 wherein the member is a robotic member having a robot hand and a robot arm.

4. The apparatus of claim 1 wherein the member is a glove box hand capable of moving in any desired direction and capable of manipulating a variety of objects including different sized objects.

5. The apparatus of claim 1 wherein a plurality of beam tubes have electron beams forming a common reactive volume.

6. The apparatus of claim 5 wherein the beam tubes are sufficient in number and arrangement to avoid shadows on specific objects placed in the reactive volume.

7. The apparatus of claim 1 further defined by a housing containing the ambient environment.

8. The apparatus of claim 7 wherein the housing has ports for insertion of material to be sterilized.

9. The apparatus of claim 1 further comprising magnetic means for steering the electron beam between the window and the plasma cloud.

10. The apparatus of claim 1 further comprising magnetic means for shaping the electron beam between the window and the plasma cloud.

11. A sterilization apparatus comprising, a chamber with ports allowing insertion of objects to be sterilized and having a gaseous environment therein, a plurality of vacuum tubes fixed relative to the chamber, each emitting an electron beam along a path into the chamber through a window separating the gaseous environment of the chamber from the vacuum of the tube, the beam paths from the tubes within a common plasma cloud stimulated by the electron beams interacting with the gaseous environment within the chamber, defining a volume associated with the plasma cloud wherein the objects to be sterilized are exposed to the plasma cloud, and at least one moveable member manipulating objects in a plurality of directions in the reactive volume wherein manipulated objects are sterilized.

12. The apparatus of claim 11 further defined by a nozzle surrounding a window end of each beam tube and injecting a gas directed at each electron beam from each tube.

13. The apparatus of claim 12 wherein the injected gas is helium.

14. The apparatus of claim 12 wherein the injected gas is argon.

15. The apparatus of claim 11 wherein the chamber is a glove box hand capable of moving in any desired direction and capable of manipulating a variety of objects including different sized objects.

16. The apparatus of claim 11 wherein the gaseous environment is an air environment.

17. The apparatus of claim 11 wherein the gaseous environment is at atmospheric pressure.

18. A sterilization apparatus comprising, a single electron beam tube having a window permitting emergence of an electron beam from said tube into an ambient gaseous environment while preserving a vacuum environment in the tube, the electron beam having a trajectory within a plasma cloud defining a reactive volume stimulated by interaction of the electron beam with the ambient environment, with a beam of energy less than 100 [kV] *keV* at the target, and a glove box hand and a robotic member having a robotic hand and a robotic arm, said glove box hand and robotic member manipulating objects, the glove box hand manipulating objects including objects that differ in variety, size and shape from the objects manipulated by said robotic hand, in a plurality of directions within the reactive volume wherein the manipulated objects are sterilized by said single electron beam tube.

* * * * *